United States Patent [19]

Sogawa et al.

[11] Patent Number: 5,158,560

[45] Date of Patent: Oct. 27, 1992

[54] LASER OPERATING DEVICE FOR INTRACAVITARY SURGERY

[75] Inventors: Ichiro Sogawa; Shin-ichiro Niwa; Koro Yotsuya; Takafumi Uemiya; Shin-ichi Kanazawa, all of Osaka, Japan

[73] Assignee: Sumitomo Electric Industries, Ltd., Osaka, Japan

[21] Appl. No.: 460,085

[22] PCT Filed: Jun. 6, 1989

[86] PCT No.: PCT/JP89/00568

§ 371 Date: Feb. 6, 1990

§ 102(e) Date: Feb. 6, 1990

[87] PCT Pub. No.: WO89/11829

PCT Pub. Date: Dec. 14, 1989

[30] Foreign Application Priority Data

Jun. 6, 1988 [JP] Japan .................. 63-138757

[51] Int. Cl.$^5$ ............................................. A61B 17/00
[52] U.S. Cl. ............................................. 606/15; 606/7; 128/673
[58] Field of Search ................ 606/2, 7, 10–17; 128/395–398, 660.03, 662.06

[56] References Cited

U.S. PATENT DOCUMENTS

| | | | |
|---|---|---|---|
| 4,576,177 | 3/1986 | Webster, Jr. | 128/660.01 |
| 4,619,268 | 10/1986 | Uphold et al. | 128/671 |
| 4,711,246 | 12/1987 | Alderson | 128/667 |
| 4,718,425 | 1/1988 | Tanaka et al. | 128/673 |
| 4,791,926 | 12/1988 | Fry | 606/7 |
| 4,799,479 | 1/1989 | Spears | 606/7 |
| 4,862,886 | 9/1989 | Clarke et al. | 606/7 |
| 4,887,605 | 12/1989 | Angelsen et al. | 128/660.03 |

FOREIGN PATENT DOCUMENTS

| | | |
|---|---|---|
| 0064352 | 11/1982 | European Pat. Off. |
| 0194856 | 9/1986 | European Pat. Off. |
| 57-66748 | 4/1982 | Japan |
| 59-46952 | 3/1984 | Japan |
| 8500510 | 2/1985 | PCT Int'l Appl. |
| 8606269 | 11/1986 | PCT Int'l Appl. |
| 8606642 | 11/1986 | PCT Int'l Appl. |

*Primary Examiner*—Peter A. Aschenbrenner
*Attorney, Agent, or Firm*—Cushman, Darby & Cushman

[57] ABSTRACT

This invention relates to an intracavitary laser operating device using a laser.

The device, has a catheter (2) accommodating laser light projecting fibers, a pulse laser oscillator device (1), an acoustic detector (4) detecting the acoustic wave generated from the diseased portion, an acoustic analyzer (5) analyzing the acoustic wave from the acoustic detector (4) and obtaining the amplitude change data and spectrum data of the acoustic wave, and a controller (7) for calculating the optimum condition of the projection of the laser light to be projected to the diseased part depending on the data from the acoustic analyzer (5) and controlling the pulse laser oscillator device (1) based on said optimum condition of the projection.

According the the device mentioned above, since the laser light can be projected to the diseased part based on the optimum condition of the projection, it is possible to avoid an occurrence of a risk that a normal blood vessel wall is damaged or carbonized or that a perforation in the blood vessel or new re-stenosis is formed.

1 Claim, 4 Drawing Sheets

LASER OPERATING DEVICE FOR INTRACAVITARY SURGERY

FIELD OF THE INVENTION

The present invention relates to a laser operating device for intracavitary surgery, and more in particular to a laser operating device for intracavitary surgery which is used for removing a diseased part inside a cavity using laser light.

BACKGROUND OF THE INVENTION

In the prior art, there have been contrived various kinds of devices for medical treatment diagnosis and methods thereof for removing, e.g. a stenosis or occlusion of a blood vessel and an atheroma due to such as an arteriosclerosis or such as calculus in a kidney or urethra.

A bypass operation is the most assured treatment method in which a lesion is completely removed by replacing a blood vessel which includes a diseased part with one of the patient's own blood vessels or with an artificial blood vessel, for example. However, since this method is followed by a surgery in which a vital organism is cut open, the vital body is subjected to a burden and a large amount of costs is needed for the treatment. Moreover, although a drug treatment is also adopted, it is effective only for solution of a thrombus and it has been difficult to remove an atheroma focus.

Therefore, there has been recently adopted a treatment that a catheter is inserted into a tubular cavity from the outside of a body and reaches a diseased part so as to directly remove a cause of an obstacle.

One treatment is performed in a manner that a balloon catheter having a balloon attached on its distal tip portion is used and the balloon expanded when it is reaches the diseased part so that the stenosis of the tubular cavity is mechanically expanded. However, since the stenosis is simply expanded, e.g. the diseased focus of the arteriosclerosis or thrombus which causes a stenosis can not be removed, a probability of a relapse of a disease in a short period is high. Moreover, in the cases that the blood vessel is entirely occluded and that the arteriosclerosis is so advanced as to cause a calcification, it becomes difficult to treat with a blood vessel.

The other treatment is a method using laser light such as YAG laser or argon laser, wherein a metallic or ceramic chip attached to the tip of the catheter is heated by the laser light irradiated from the tip of an optical fiber so that the heated chip is pressed onto the diseased part so as to burn out the diseased part. According to this method, though the diseased part can be removed, the control of the light heating power is difficult and if the chip is overheated, a normal vessel wall is damaged or carbonized so that there may occur a new risk of vascular perforation or a new re-stenosis. Moreover, in case the vessel is tortuous or completely occluded, it is not available because the chip can not be inserted.

Therefore, it is also adopted that the laser light from such as YAG laser, argon laser or excimer laser is projected to the diseased part from the tip of the fiber so as to vaporize the diseased part directly. Since the laser light directly vaporizes the projected portion, the laser light is available also for a completely occluded diseased part. And since the output of the laser can be controlled, upon controlling the amplitude, pulse width and pulse intervals of the pulse laser, it is possible to control the power with high accuracy.

By the way, in the intracavitary laser operating device of a direct irradiation type mentioned above, the operator controls the output of the laser light source or controls the amplitude, pulse width and pulse intervals in the case of a pulse laser according to the sort of the diseased part such as atheroma, thrombus and carbonization and to the degree of the advance of the disease state, whereby the power control is performed, but it has been impossible to control the power while confirming the state of the diseased part during the irradiation of the laser.

With further detailed description, since there is a fear of damaging the cavity if a big power is abruptly projected to the diseased part by using the catheter mentioned above, it is necessary to divide the power of the laser light into several grades so as to be gradually raised up. In this case, it is necessary to confirm the changing condition of the diseased part by, e.g., endoscopic fibers every time the power is raised up, so that it takes much time and labor.

The present invention has been made considering the problem mentioned above and has its object to provide an intracavitary laser operating device in which the power control can be performed confirming the state of the diseased part during the irradiation of the laser.

DISCLOSURE OF THE INVENTION

In order to accomplish the object mentioned above, the intracavitary laser operating device of the present invention is an operating device for projecting laser light to a diseased part through laser light projecting fibers by inserting a catheter accommodating the laser light projecting fibers into a cavity, comprising;

a pulse laser oscillator for generating laser light of a predetermined cycle and applying to optical fibers, an acoustic wave receiver for detecting an acoustic wave generated from a diseased portion in response to the projection of the pulse laser, an acoustic analyzer for analyzing the acoustic wave from the acoustic receiver and obtaining the amplitude changing data and spectral data of the acoustic wave, and a controller for calculating the optimum condition of the projection of the laser light to be projected to the diseased part based on the data from the acoustic analyzer and for controlling said pulse laser oscillator depending on said optimum projection condition.

According to the present invention as described above, when the catheter accommodating the laser light projecting fibers is inserted into the cavity so that the laser light is projected to the diseased part through the laser light projecting fibers, a sonic wave is generated from the diseased part because of the thermal expansion caused by a sudden heat absorption at a neighborhood of a vaporization starting portion of the diseased part in accordance with the output projection of the pulse laser and the generation of the sonic wave can be detected by the acoustic wave detecting unit. The acoustic wave is analyzed by the acoustic analyzer so as to obtain the amplitude changing data and the spectral data of the acoustic wave. Subsequently, in the controller, the optimum projection condition of the laser light (amplitude, pulse width and pulse intervals) to be projected to the diseased part depending on the data from the acoustic analyzer is calculated and the pulse laser oscillator is controlled depending on said optimum projection condition, whereby the laser light can be projected to the diseased part under the optimum condition of the projection.

Accordingly there can be avoided a fear that, a normal blood vessel wall is damaged or carbonized resulting in occurrence of a risk of a perforation of a blood vessel or new re-stenosis.

OPTIMUM EMBODIMENT OF THE INVENTION

An embodiment of the present invention is explained hereinafter with reference to the drawings.

Figure 1:
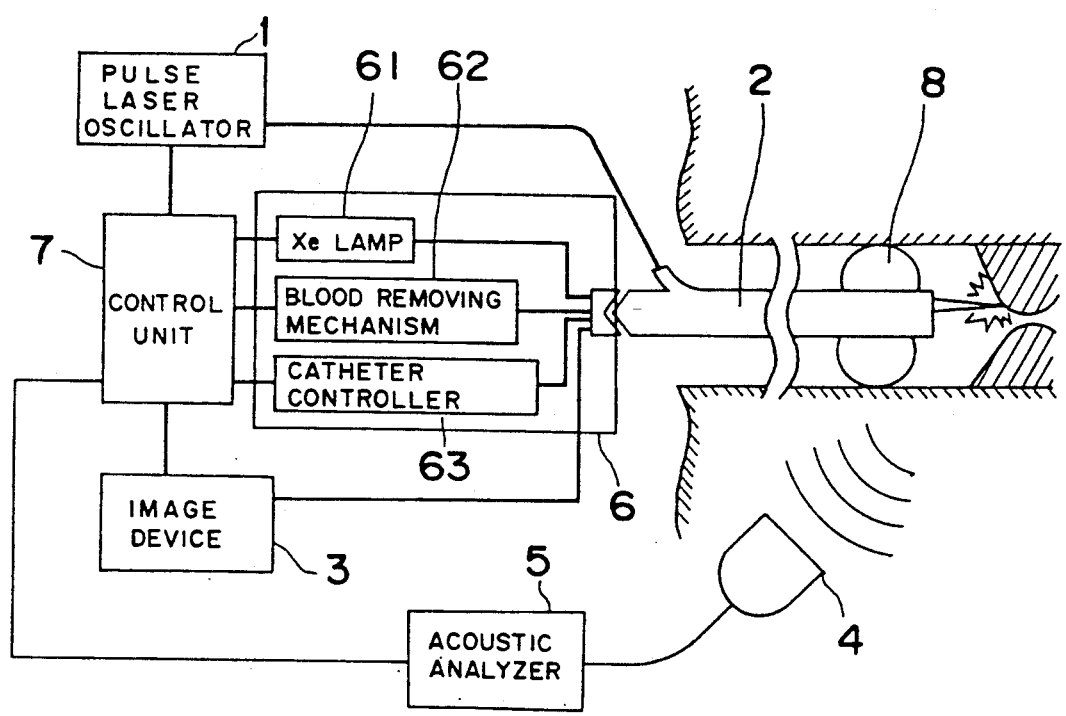
FIG. 1 is a schematic diagram showing an embodiment of an intracavitary laser operating device.

As shown in FIG. 1, the intracavitary laser operating device of the present embodiment comprises a pulse laser oscillator (1), a catheter (2) for operation accommodating endoscopic fibers for endoscopy of a diseased part, illumination light guide, flush liquid passage hole, balloon dilation liquid passage hole, laser light projecting fibers and tip portion control wire, image device (3) for displaying a form of an endoscopic image and a fluorescent spectrum analysis and recording the image data, acoustic detector (4) for receiving an acoustic wave generated from the diseased part in accordance with the laser projection, acoustic analyzer (5) for analyzing the wave from the acoustic receiver and obtaining the amplitude changing data of the acoustic wave and the spectral data, and comprising a controller (7) for controlling the application of the light to said catheter (2) through an interface (6) and controlling the charge of the liquid and for calculating the optimum projection condition (amplitude, pulse width and pulse interval) of the laser light to be projected to the diseased part depending on the data from the acoustic analyzer (5) and controlling said pulse laser oscillator based on said optimum projection condition. Moreover, (8) denotes a balloon for stopping a blood flow to be fixed, which is attached to the distal portion of the catheter (2).

The above mentioned acoustic detector (4) comprising a microphone detects an acoustic wave generated from the diseased part because of the thermal expansion caused by the sudden thermal absorption at the neighborhood of the vaporization starting portion by receiving the laser projection onto the diseased tissue.

The above mentioned acoustic analyzer (5) removes a noise such as a heart beat from the acoustic waves detected by the acoustic detector (4) and analyzes the signals without the noise, thereby obtaining the amplitude changing data and spectral data.

Figure 2:
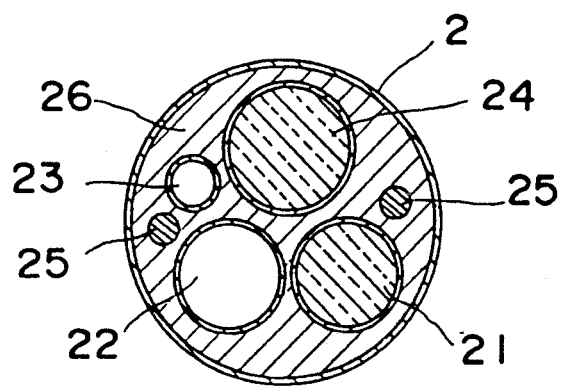
FIG. 2 is a sectional view of a catheter.

FIG. 2 is a sectional view of the catheter (2), wherein the endoscopic fibers (21), flush liquid passage hole (22), balloon dilation liquid passage hole (23), laser light projecting fibers (24) and tip portion control wire (25) are bundled and fixed in a transparent medium (26) and the surface thereof is coated by a thin film. Moreover, the above transparent medium (26) also serves as an illumination light guide.

The endoscopic fiber (21) is made of materials having little dispersion, accomplishing the high accuracy of the both edge optical systems particularly in order to accomplish the high quality of the image forming. Since in the present embodiment is used an excimer laser of a pulse laser in the range of an ultraviolet rays in which a diseased focus can be removed with good efficiency and in safety, therefore the laser light projecting fiber (24) is made of materials such as quartz with good transmittance through which ultraviolet rays can be transmitted with high energy density and with low loss and the end surface thereof is processed with high accuracy in order to suppress the heat generation at the end surface. The transparent medium (26) as the illumination light guide is made of visible light transmittable materials with good flexibility such as multi-components group glass, plastic resin and rubber and the illumination light is projected from the tip section of the catheter (2). The tip of the catheter is guided to the diseased part by the tip control wire which is controlled by a catheter controller (63) mentioned later in order that the edge portion of the catheter (2) is opposed to the diseased part.

The outer diameter of the catheter (2) accommodating the respective components (21) to (26) mentioned above is made extremely thinned diameter of a few milli meters, preferably less than 1.5 mm. Therefore, it becomes possible to easily reach any part in the blood vessel by the guide of the catheter controller (63).

Figure 3:
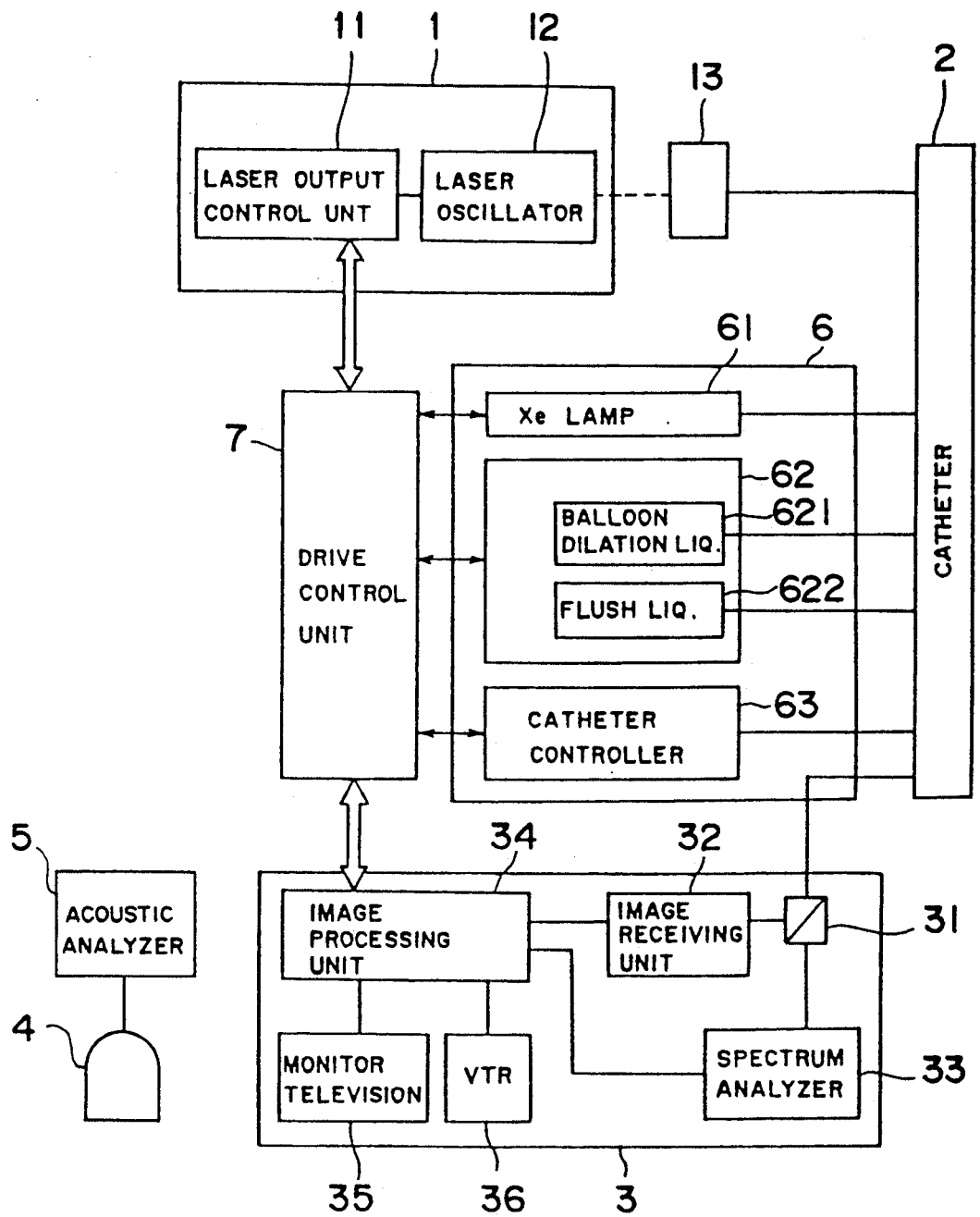
FIG. 3 is a block diagram showing, e.g., a pulse laser oscillator, controller and image device of the intracavitary laser operating device.

FIG. 3 is a diagram showing the details of the pulse laser oscillator (1), interface portion (6), controller (7) and image device (3) mentioned above. The pulse laser oscillator (1) comprises a laser output control unit (11) and laser oscillating unit (12), wherein the laser output control unit (11) controls the power of the laser light projected from the laser oscillating unit (12). Since the laser oscillating unit (12) is composed of a pulse laser in a range of ultraviolet rays which is absorbed largely by the tissue and has a large peak power, the diseased part can be removed with good efficiency and in safety. Therefore, the laser oscillating unit is composed of a pulse oscillation excimer laser of noble gas halide such as XeCl, KrF and ArF. Moreover, (13) denotes a connecting portion for connecting the projected laser light to the light leading fiber (24), which is composed of a minute optical system having little loss.

The interface portion (6) comprises; a Xe lamp (61) for applying visible light to said illumination light guide (26), a blood removing mechanism (62) for charging balloon dilation liquid (621) (such as isotonic sodium chloride solution) and flush liquid (622) (liquid having little loss in the range of the wave length of the used laser) into the balloon dilation fluid passage hole (23) and flush liquid passage hole (22), and a catheter controller (63) having an operation mechanism for operating the control wire (25), which are respectively controlled by the controller (7). That is to say, the controller (7) drives the catheter controller (63) so as to reach the catheter (2) to a desired portion, thereby performing the ON/OFF control of the Xe lamp (61) and the control of the blood removing mechanism (62).

The controller (7) also judges the sort of the diseased tissue and the degree of the progress of the disease depending on the amplitude changing data and spectrum data from the acoustic analyzer (5) and calculates the optimum irradiation condition (amplitude, pulse width and pulse interval) in accordance with the degree of the progress of the disease and transmits a control signal to the laser output control unit (11) depending on the optimum output data, thereby controlling the output level (10 mJ/pulse to 500 mJ/pulse), pulse width (2 nsec to 1 μsec degree) and pulse repeating frequency (10 to 200 Hz degree) of the laser output.

The image device (3) comprises a division optical system (31) dividing image light generated from the endoscopic fibers (21), image receiving unit (32) receiving one of the divided light by CCD elements, spectrum analyzing unit (33) obtaining the components of the fluorescent spectrum of the other divided light, image processing unit (34) compensating the output signals of the image receiving unit (32) and the spectrum analyzing unit (33), monitor television (35) displaying the processed image signal on the screen of the television, and VTR (36) for recording the image.

Figure 4:
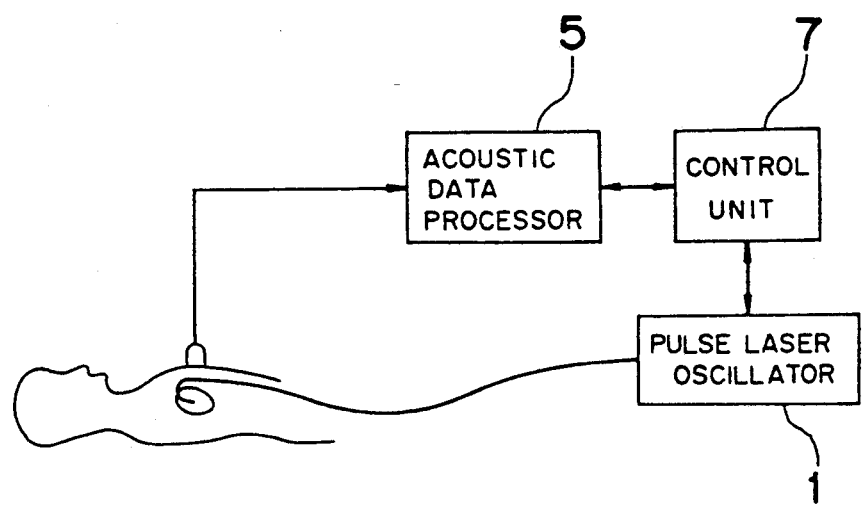
FIG. 4 is a schematic diagram showing an example of said intracavitary laser operating device applied to a human body.

FIG. 4 is a schematic diagram showing an example of the above mentioned intracavitary laser operating device applied to a human body, wherein the catheter (2) is inserted to a thrombus formed portion in a coronary artery and the acoustic detector (4) is situated on the surface of the body nearest to the thrombus portion. The laser light is projected to the thrombus from the pulse laser oscillator (1) through the laser projecting fibers (24) in the catheter (2). The acoustic detector (4) detects the acoustic wave which is generated from the diseased part because of the thermal expansion caused by the sudden heat absorption in the neighborhood of the vaporization starting portion due to receiving the laser irradiation by the diseased tissue. Subsequently, the acoustic analyzer (5) removes a noise such as a heart beat from the acoustic waves detected by the acoustic detector (4) and analyzes the signal without a noise, thereby obtaining the amplitude changing data and spectrum data. Subsequently, the controller calculates the optimum irradiation condition of the laser light to be irradiated to the diseased part depending on the data from the acoustic analyzer (5) so as to control the pulse laser oscillator mentioned above.

Figure 5:
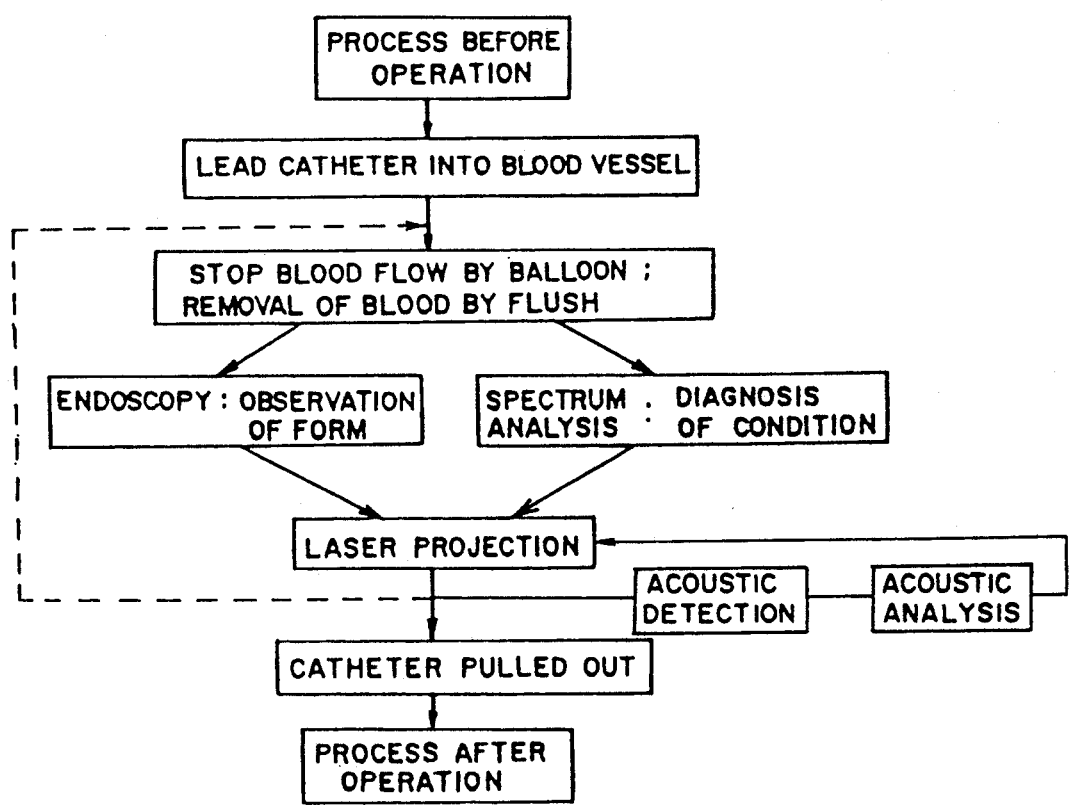
FIG. 5 is a flow chart showing the operational process of the intracavitary laser operating device.

Next, the operating process of the above mentioned intracavitary laser operating device is explained with reference to FIG. 5. First, as the process before operation, after the disinfection of the catheter inserting portion, anesthetization and supply of the catheter are performed, the catheter controller (63) is driven through the drive controller (7) so that the catheter (2) is guided into a predetermined blood vessel (such as a coronary artery). Subsequently, the balloon dilation liquid (621) is charged into the balloon dilation fluid passage hole (23) so that the balloon (8) is expanded for stopping the blood flow and the tip of the catheter (2) is fixed in the blood vessel by the balloon (8). Subsequently, the flush liquid (622) is immediately charged into the flush liquid passage hole (22) so that the blood in the lower stream below the hemostasis portion is replaced to be made transparent. Upon observing by the monitor television (35), it is examined whether or not there is a diseased part, and if there is no diseased part, the balloon (8) is constricted to recover the flow of the blood and the catheter (2) is advanced to the other portion. If there is a diseased part, the pulse laser oscillator (1) is driven and the laser light is projected to the diseased part. When the diseased part receives the projection of the pulse laser light, the acoustic wave is generated because of the thermal expansion caused by the sudden heat absorption at the neighborhood of the vaporization starting portion. The generated acoustic wave is detected by the acoustic detector (4) and analyzed by the acoustic analyzer (5), thereby obtaining the amplitude changing data of the acoustic wave and spectrum data. Subsequently, the controller (7) judges the sort of the diseased tissue and the degree of the progress of the disease depending on the amplitude changing data and the spectrum data and calculates the optimum irradiation condition in accordance with the sort of the diseased tissue and the progress degree of the disease, so that the laser light is projected to the diseased part under controlling the amplitude, pulse width and pulse intervals of the laser light depending on the calculated data.

The processes as mentioned above are repeated until the diseased part is completely destroyed. If the diseased part is completely destroyed, the balloon (8) is constricted and the blood flow is recovered and then the catheter (2) is pulled out. Subsequently, a necessary process after operation is performed and the operation is finished.

In addition, in this embodiment, though the acoustic detector is provided outside the body, the acoustic detector can be attached to the tip of the catheter. In this case, the acoustic detector can be provided also as a sensor for measuring blood pressure, and since it is possible to detect the change of the blood pressure caused by the removal of the diseased part, not only the laser projection can be performed in safety but also the effect of the treatment can be confirmed, that is still more effective. As an acoustic detector, there may be used a semiconductor pressure sensor, piezoelectric elements or optical fiber pressure sensor having a diaphragm provided on the tip of the optical fiber. Moreover, though the explanation is made about the intravascular treatment in this embodiment, it is also possible to apply the device to the other treatments such as using the laser to destroy a calculus in urethra by using a similar device.

As described above, according to the present invention, since in the case that, the catheter accommodating the endoscopic fibers and laser light projecting fibers is inserted into the cavity and the diseased part in the cavity is searched by the endoscopic fibers so that the laser light is projected to the diseased part through the laser light projecting fibers, it is possible to calculate the optimum irradiation condition of the laser light to be projected to the diseased part depending on the change of the acoustic wave from the diseased part so as to project the laser light to the diseased part based on said optimum irradiation condition, therefore, obtaining a specific effect of avoiding a fear that a normal blood vessel wall is damaged or carbonized or that a risk of a perforation in a blood vessel or a new re-stenosis is caused.

What is claimed is:

1. An intracavitary laser operating device for projecting laser light to a diseased part through laser light projecting fibers by inserting a catheter accommodating said laser light projecting fibers into a cavity, comprising:

pulse laser oscillator means for generating laser light of a predetermined cycle;
optic fiber means for receiving said laser light and for supplying said light to said diseased part;
acoustic receiver means for detecting an acoustic wave generated from the diseased part;
acoustic analyzer means, operatively coupled to said acoustic receiver means, for analyzing the acoustic wave detected by said acoustic receiver means and for obtaining amplitude change data and spectrum data of the acoustic wave; and controller means, operatively coupled to said acoustic analyzer means and to said pulse laser oscillator means, for calculating an optimum condition of the laser light depending on said amplitude change data and said spectrum data from said acoustic analyzer and for controlling said pulse laser oscillator device based on said optimum condition of the laser light;

wherein said catheter has a tip portion, said tip portion having a side, said acoustic receiver is provided on the side of the tip portion, and said acoustic receiver means comprises measurement means for measuring blood pressure.

* * * * *